US006947132B1

(12) United States Patent
Boss et al.

(10) Patent No.: US 6,947,132 B1
(45) Date of Patent: Sep. 20, 2005

(54) THERMO-ELECTRICALLY COOLED SURFACE-ENHANCED RAMAN SPECTROSCOPY SENSOR SYSTEM TO DETECT VOLATILE ORGANIC COMPOUNDS

(75) Inventors: Pamela A. Boss, San Diego, CA (US); Stephen H. Lieberman, La Mesa, CA (US); John M. Andrews, San Diego, CA (US); Gregory Wayne Anderson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 325 days.

(21) Appl. No.: 10/413,188

(22) Filed: Apr. 14, 2003

Related U.S. Application Data

(63) Continuation-in-part of application No. 10/133,705, filed on Apr. 26, 2002, and a continuation-in-part of application No. 09/888,737, filed on Jun. 25, 2001, now Pat. No. 6,888,629, and a continuation-in-part of application No. 09/805,665, filed on Mar. 13, 2001, now Pat. No. 6,614,523, and a continuation-in-part of application No. 09/593,675, filed on Jun. 14, 2000, now Pat. No. 6,406,777.

(51) Int. Cl.[7] .................................................. G01J 3/44
(52) U.S. Cl. .................................................. 356/301
(58) Field of Search .................................................. 356/301

(56) References Cited

U.S. PATENT DOCUMENTS 5,255,067 A * 10/1993 Carrabba et al. ........... 356/301

OTHER PUBLICATIONS

Easley et al., Enhanced adsorbate Raman scattering from pyridine on silver in ultrahigh vacuum, American Vacuum Society, pp. 629-632, Mar. 1981.*

Dick et al., Metal Film over Nanosphere (MFON) Electrodes for Surface Enhanced Raman Spectroscopy (SERS): Improvements in Surface Nanostructure Stability and Suppressio of Irreversible Loss, American Chemical Society, pp. 853-859, published Dec. 27, 2001.*

Litorja et al., Surface Enhanced Raman Scattering Detected Temperature Programmed Desorption: Optical Properties, Nanostructures, and Stability of Silver Film over SIO Nanosphere Surfaces, American Chemical Society, pp. 6907-6915, Jun. 16, 2001.*

* cited by examiner

*Primary Examiner*—Zandra V. Smith
(74) *Attorney, Agent, or Firm*—Peter A. Lipovsky; Michael A. Kagan; Allan Y. Lee

(57) ABSTRACT

A thermoelectrically cooled surface-enhanced Raman spectrometer sensor system and method for monitoring of volatile organic compounds in gas, liquid, and soil environments. The sensor system comprises a means for providing an inert gas, a thermal desorption tube containing an adsorbate, and a sample chamber with a SERS structure. For liquid and soil environments, the sensor system also comprises a manifold having a semipermeable membrane for separating moisture from an analyte. An optical module mounted to the sample chamber directs an optical excitation signal for irradiating the SERS structure and receives a SERS optical emissions signal. Such optical emissions signal may be detected by a spectroanalysis system and correlated to a particular analyte by a control processor, which generates an alert signal containing a message that the presence of analyte has been detected. The control processor may also activate warning device, such as an audible siren or a visual alarm.

19 Claims, 3 Drawing Sheets

THERMO-ELECTRICALLY COOLED SURFACE-ENHANCED RAMAN SPECTROSCOPY SENSOR SYSTEM TO DETECT VOLATILE ORGANIC COMPOUNDS

CROSS REFERENCE TO RELATED APPLICATIONS

This application is a continuation-in-part of commonly assigned U.S. patent application Ser. No. 10/133,705, entitled THERMO-ELECTRICALLY COOLED SURFACE ENHANCED RAMAN SPECTROSCOPY SENSOR SYSTEM, filed 26 Apr. 2002, a continuation-in-part of commonly assigned U.S. patent application Ser. No. 09/888,737, now U.S. Pat. No. 6,888,629 entitled SENSOR FOR PERFORMING SURFACE ENHANCED RAMAN SPECTROSCOPY AND METHOD FOR ACHIEVING SAME, filed 25 Jun. 2001, a continuation-in-part of commonly assigned U.S. patent application Ser. No. 09/805,665, now U.S. Pat. No. 6,614,523 entitled SENSOR FOR PERFORMING SURFACE ENHANCED RAMAN SPECTROSCOPY, filed 13 Mar. 2001, and a continuation-in-part of commonly assigned U.S. patent application Ser. No. 09/593,675, now U.S. Pat. No. 6,406,777 entitled A METAL AND GLASS STRUCTURE FOR USE IN SURFACE ENHANCED RAMAN SPECTROSCOPY AND METHOD FOR FABRICATING SAME, filed 14 Jun. 2000, and which are hereby incorporated by reference.

BACKGROUND OF THE INVENTION

The invention relates generally to the fields of Raman spectroscopy. More specifically, the invention relates to a sensor system that may be used for long-term, continuous monitoring of volatile organic compounds (VOCs) in gas, liquid, and soil environments.

Raman spectroscopy is an emission technique that involves inelastic scattering of incident laser energy resulting in spectral peaks that are frequency shifted from the incident energy. The Raman bands arise from changes in the polarizability in a molecule during vibration. As a result, virtually all organic molecules display a characteristic Raman emission. Therefore, a Raman sensor would not be limited to a specific class of molecules as is the case for the laser induced fluorescence (LIF) sensor. Raman spectroscopy allows the fingerprinting of species present and is structurally specific. The inherently high resolution of Raman spectra often permits the analysis and identification of several components in a mixture simultaneously.

The advent of inexpensive portably Raman spectrometers has seen renewed interest in the area of Raman spectrometry. This new generation of spectrometers employs fiber optic probes, holographic notch filters for rejection of the Rayleigh line, a single grating monochromator, and a charge-coupled device (CCD) detector for multi-channel detection. These spectrometers contain a minimum of optical components as compared to convention Raman instrumentation resulting in a high data throughput and, once coupled to a laser and spectrometer, optical fiber probes require no further alignment.

Despite the advantages of Raman spectroscopy over other spectroscopic techniques and the technological advances in the area of Raman spectrometry, Raman spectroscopy is inherently an insensitive technique. To achieve detection limits in the low ppm range would require either the use of a multiple pass cell or long acquisition times. In the 1970s, it was discovered that Raman scattering from molecules adsorbed on such noble metals as silver, copper, and gold can be enhanced by as much as $10^6$ to $10^7$. This phenomenon, called surface enhanced Raman spectroscopy (SERS), is still not understood despite intensive theoretical and experimental research. It is believed that more than one mechanism is involved in the SERS phenomenon. Initially, the SERS technique was used as a means to probe adsorption at metal interfaces both in electrochemical and gas-phase environments. This technique has proven useful in deducing the effects of interfacial structure and reactivity on the adsorption process. However, the sensitivity of the technique, as well as its exceptional spectral selectivity, has made SERS attractive for a broad range of analytical applications. SERS can be used for trace organic analysis and as a detection method in gas chromatography, liquid chromatography, and thin layer chromatography. Electrochemical SERS and SERS of chemically modified surfaces have been used to detect aromatic compounds and chlorinated hydrocarbons, organic contaminants of environmental concern in the ppm concentration range.

There are many applications in which long-term and continuous detection of particular chemical species or analytes is desirable as, for example, hydrocarbons that may be present in ground water, toxic vapors in industrial environments, explosives, metal ions, narcotics, toxic anions, and chemical warfare agents.

SUMMARY OF THE INVENTION

The invention relates generally to the fields of Raman spectroscopy. More specifically, the invention relates to a sensor system that may be used for long-term, continuous monitoring of VOCs in gas, liquid, and soil environments.

In one embodiment, the thermoelectrically cooled surface-enhanced Raman spectrometer sensor system includes a gas source for providing an inert gas into a manifold having a semipermeable membrane, which minimizes the introduction of moisture and debris into the manifold. As inert gas flows through the manifold, negative pressure causes the analyte, which may be a gas or vapor, to be drawn into the manifold through the semipermeable membrane. The analyte and inert gas mix to create a gas mixture in the manifold. The semipermeable membrane may be heated to increase the volatility of the analyte, especially when the semipermeable membrane is in contact with liquid environments such as aqueous or saturated soil environments.

Low concentrations of VOCs (ppb concentration range) may require preconcentration. A thermal desorption tube containing an adsorbate is coupled to the manifold and preconcentrates the gas mixture. Once preconcentrated, the thermal desorption tube is heated, using well-known techniques in the art, to release the gas mixture into the sample chamber.

The sample chamber includes a SERS structure that is mounted to a thermoelectric (TEM) cooler. Controlling the temperature of TEM cooler allows specific analytes to be condensed onto the SERS structure because different analytes condense at different temperatures.

An optical energy source, such as a laser, generates an optical excitation signal that is focused into an optical fiber coupled to an optical module. The optical module directs and focuses the optical excitation signal to irradiate the SERS structure.

The irradiation of the SERS structure by the optical excitation signal in the presence of specific analytes in the gas mixture causes the generation of surface enhanced Raman scattering (SERS) optical emissions signal. The spectral characteristics of the SERS optical emissions signal are detected by a spectroanalysis system and provided to a control processor for recording and analysis. The control processor may also transmit the SERS optical emissions signal detected by spectroanalysis system to a remote processor. When the presence of specific analytes in the gas mixture is detected, i.e., a specific analyte is in contact with the SERS structure, the control processor generates an alert signal containing a message that a specific analyte has been detected, which may then be transmitted to the remote processor or another processor. The control processor may also activate a warning device, such as an audible siren or a visual alarm.

In another embodiment, the thermo-electrically cooled surface-enhanced Raman spectrometer sensor system includes a gas source for providing an inert gas is coupled to a thermal desorption tube containing an adsorbate. The sensor system of this embodiment may used for monitoring of VOCs in gas environments.

It is within the embodiment of the thermoelectrically cooled surface-enhanced Raman spectrometer sensor system to have a plurality of sample collectors monitoring the VOCs in the same location. It is also within the embodiment of the thermoelectrically cooled surface-enhanced Raman spectrometer sensor system to have a plurality of sample collectors monitoring several locations at the same time.

BRIEF DESCRIPTION OF THE DRAWINGS

For a more complete understanding of the thermo-electrically cooled surface-enhanced Raman spectrometer sensor system, reference is now made to the following detailed description of the embodiments as illustrated in the accompanying drawings, wherein.

DESCRIPTION OF THE EMBODIMENTS

Figure 1:
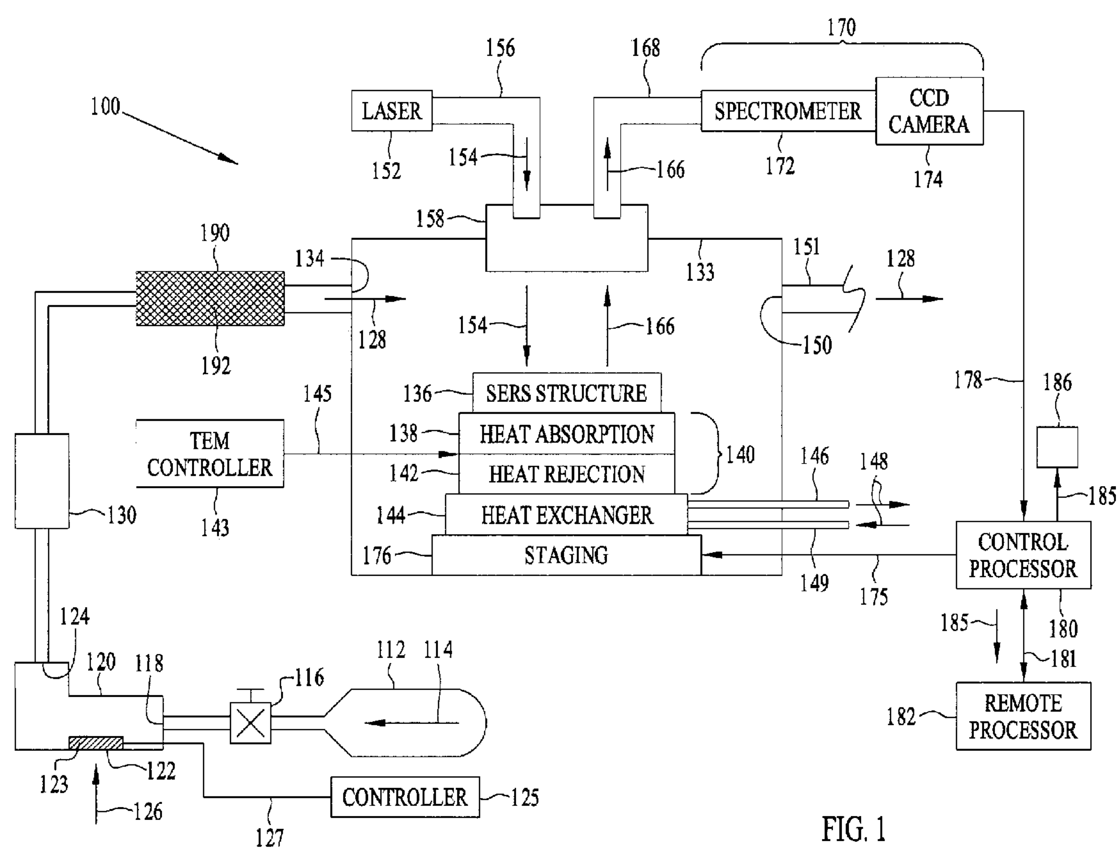
FIG. 1 is a block diagram of the thermoelectrically cooled surface-enhanced Raman spectrometer sensor system.

The thermoelectrically cooled surface-enhanced Raman spectrometer sensor system is described with reference to FIG. 1. Controlling the temperature of thermoelectric (TEM) cooler 140 facilitates condensation of selected analytes 126 that may be present in sample chamber 133, so that they may condense onto SERS structure 136, because different analytes condense at different temperatures. When in contact with each other, analyte 126 and SERS structure 136 may be stimulated by optical excitation signal 154 to produce optical emissions signal 166, which is unique to a particular analyte. Such optical emissions signal 166 may be detected by spectroanalysis system 170 and then correlated to the particular analyte 126 by control processor 180. Control processor 180 may transmit the SERS optical emissions signal 166 detected by spectroanalysis system 170 to remote processor 182 via signal line 181. When an analyte is in contact with the SERS structure 136, control processor 180 also generates alert signal 185 containing a message that the presence of analyte 126 has been detected, which may then be transmitted to remote processor 182 or another processor. Control processor 180 may also activate warning device 186, such as an audible siren, a visual alarm, and the like, via alert signal 185.

Still referring to FIG. 1, sensor system 100 includes a gas source 112 for providing an inert gas 114 such as diatomic nitrogen ($N_2$) under the control of valve 116 through input port 118 into manifold 120. Manifold 120 includes analyte input port 122, in which semipermeable membrane 123 is mounted, and output port 124. Semipermeable membrane 123, which may be immersed in gas, liquid, or soil environments, minimizes the introduction of moisture and debris into manifold 120.

As inert gas 114 flows over analyte input port 122 and through manifold 120, negative pressure causes analyte 126, which may be a gas or vapor, to be drawn into manifold 120 through semipermeable membrane 123. Analyte 126 and inert gas 114 mix to create gas mixture 128 in manifold 120. Semipermeable membrane 123 may be heated under the supervision of controller 125 via signal line 127 in order to increase the volatility of analyte 126, especially when semipermeable membrane 123 is in contact with liquid environments such as aqueous or saturated soil environments. Gas mixture 128 flows out of output port 124 and through desiccant chamber 130, which removes moisture that may have passed through semipermeable membrane 123 from gas mixture 128.

Low concentrations of VOCs (ppb concentration range) may require preconcentration. After passing through desiccant chamber 130, gas mixture 128 flows through thermal desorption tube 190 that contains adsorbate 192, which will preconcentrate gas mixture 128. Once preconcentrated, thermal desorption tube 190 is heated, using well-known techniques in the art, to release gas mixture 128 into sample chamber 133 via input port 134. Gas mixture 128 is vented from sample chamber 133 through outlet tube 151 via output port 150.

Sample chamber 133 includes SERS structure 136 that is mounted to the heat absorption side 138 of TEM cooler 140. SERS structure 136 is immersed within and in intimate contact with gas mixture 128 when gas mixture 128 fills sample chamber 133.

TEM cooler 140 also includes heat rejection side 142 for rejecting heat absorbed from SERS structure 136 by heat absorption side 138. TEM controller 143 via signal line 145 controls the temperature of TEM cooler 140 and hence, SERS structure 136. Controlling the temperature of TEM cooler 140 allows specific analytes to be condensed onto SERS structure 136 because different analytes condense at different temperatures. For example, vapor condensation of benzene occurs at 15° C., toluene at 9° C., and MTBE at −5° C. for a SERS substrate coated with 1-propanethiol.

Heat rejection side 142 of TEM cooler 140 is mounted to heat exchanger 144, which transfers heat energy absorbed from heat rejection side 142 of TEM cooler 140 out of sample chamber 133. By way of example, heat exchanger 144, which may be a gas or liquid heat exchanger, may have a fluid inlet tube 149 for receiving fluid 148 that is relatively cool for absorbing heat energy from heat rejection side 142 of TEM cooler 140, and an outlet tube 146 through which heated fluid 148 flows out of heat exchanger 144. Fluid 148 may be either a gas (such as air) or a liquid (such as water). However, it is to be understood that fluid 148 may include gases and liquids other than those specifically identified herein.

An optical energy source, such as laser 152, generates a monochromatic and coherent optical excitation signal 154 that is focused into optical fiber 156 coupled to optical module 158. Optical module 158 directs and focuses optical excitation signal 154 to irradiate SERS structure 136. Optical module 158 also filters out any Raman emissions that may result from optical excitation signal 154 propagating through optical fiber 156.

The irradiation of SERS structure 136 by optical excitation signal 154 in the presence of analyte 126 in gas mixture 128 causes the generation of surface enhanced Raman scattering (SERS) optical emissions signal 166. Optical module 158 includes a lens (not shown) for gathering and directing some of such SERS optical emissions signal 166 into optical fiber 168. Optical module 158 also prevents optical excitation signal 154 from entering optical fiber 168 and thereby prevents the stimulation of Raman emissions therein. By way of example, optical excitation signal 154 preferably has a wavelength in the range of about 633 nm to about 852 nm. Longer wavelengths of optical excitation signal 154 in the near-infrared range provide a better SERS response, i.e., greater output of optical emissions signal 166. Longer wavelengths of optical excitation signal 154 also reduce fluorescence interference with optical emissions signal 166.

Optical emissions signal 166 is propagated via optical fiber 168 to spectroanalysis system 170, which may include spectrometer 172 and charge-coupled device (CCD) camera 174. Spectroanalysis system 170 detects the spectral characteristics of SERS optical emissions signal 166, which are then provided to control processor 180 for recording and analysis via signal line 178. Control processor 180 may transmit the SERS optical emissions signal 166 detected by spectroanalysis system 170 to remote processor 182 via signal line 181. Remote processor 182 may also be used as a backup processor for control processor 180. When the presence of analyte 126 in gas mixture 128 is detected, i.e., analyte 126 is in contact with the SERS structure, control processor 180 generates alert signal 185 containing a message that analyte 126 has been detected, which may then be transmitted to remote processor 182 or another processor. Control processor 180 may also activate warning device 186, such as an audible siren, a visual alarm, and the like, via alert signal 185.

Heat exchanger 144 may be mounted on a staging apparatus 176 for positioning SERS structure 136 at selected positions or coordinates with respect to the propagation path of optical excitation signal 154. Staging apparatus 176 may be controlled by control processor 180 via signal line 175 and may be implemented as a one-dimensional (X), two-dimensional (X,Y), or three-dimensional (X,Y,Z) positioning system, where X, Y, and Z represent coordinates on mutually orthogonal axes.

Figure 2:
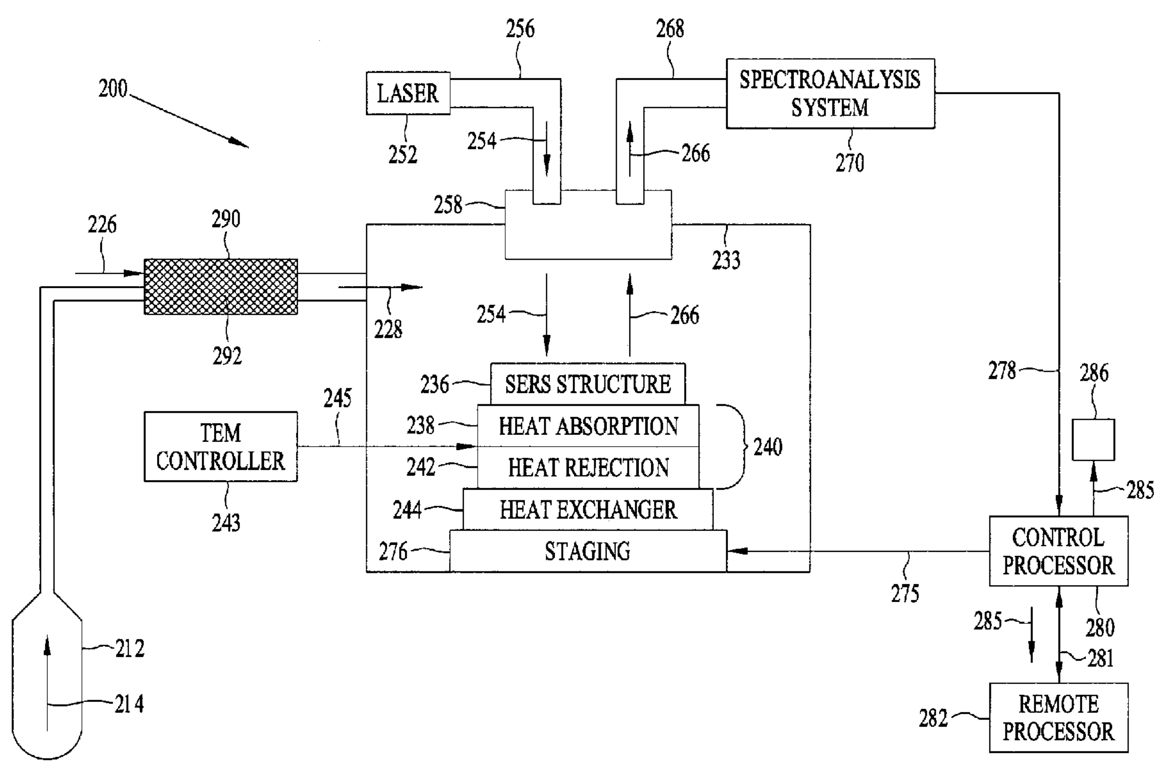
FIG. 2 is a block diagram of the thermoelectrically cooled surface-enhanced Raman spectrometer sensor system used to monitor for VOCs in the gas phase; and (c)

FIG. 2 shows another embodiment of the thermoelectrically cooled surface-enhanced Raman spectrometer sensor system. In this embodiment, sensor system 200 is used to monitor for VOCs in the gas phase. Sensor system 200 includes a gas source 212 for providing an inert gas 214 such as diatomic nitrogen ($N_2$). Analyte 226 and inert gas 214 mix to create gas mixture 228 in thermal desorption tube 290 that contains adsorbate 292. Thermal desorption tube 290 is then heated, using well-known techniques in the art, to release gas mixture 228 into sample chamber 233. SERS structure 236 is immersed within and in intimate contact with gas mixture 228 when gas mixture 228 fills sample chamber 233.

TEM controller 243 via signal line 245 controls the temperature of TEM cooler 240 and hence, SERS structure 236. Heat rejection side 242 of TEM cooler 240 rejects heat absorbed from SERS structure 236 by heat absorption side 238. Heat exchanger 244 transfers heat energy absorbed from heat rejection side 242 of TEM cooler 240 out of sample chamber 233.

Laser 252 generates a monochromatic and coherent optical excitation signal 254 that is focused into optical fiber 256 coupled to optical module 258. Optical module 258 then directs and focuses optical excitation signal 254 to irradiate SERS structure 236. The irradiation of SERS structure 236 by optical excitation signal 254 in the presence of analyte 226 in gas mixture 228 causes the generation of SERS optical emissions signal 266. Optical module 258 gathers and directs some of such SERS optical emissions signal 266 into optical fiber 268. Optical emissions signal 266 is propagated via optical fiber 268 to spectroanalysis system 270 that detects the spectral characteristics of SERS optical emission 266, which are then provided to control processor 280 for recording and analysis via signal line 278 and/or to remote processor 282 via signal line 281. Remote processor 282 may also be used as a backup processor for control processor 280. When the presence of analyte 226 in gas mixture 228 is detected, i.e., analyte 226 is in contact with the SERS structure, control processor 280 generates signal 285 containing a message that the presence of analyte 226 has been detected, which may then be transmitted to remote processor 282 or another processor. Control processor 280 may also activate warning device 286, such as an audible siren, a visual alarm, and the like, via alert signal 285.

Control processor 280, via signal line 275, may also control staging apparatus 276, which positions SERS structure 236 at selected positions or coordinates with respect to the propagation path of optical excitation signal 254.

Figure 3:
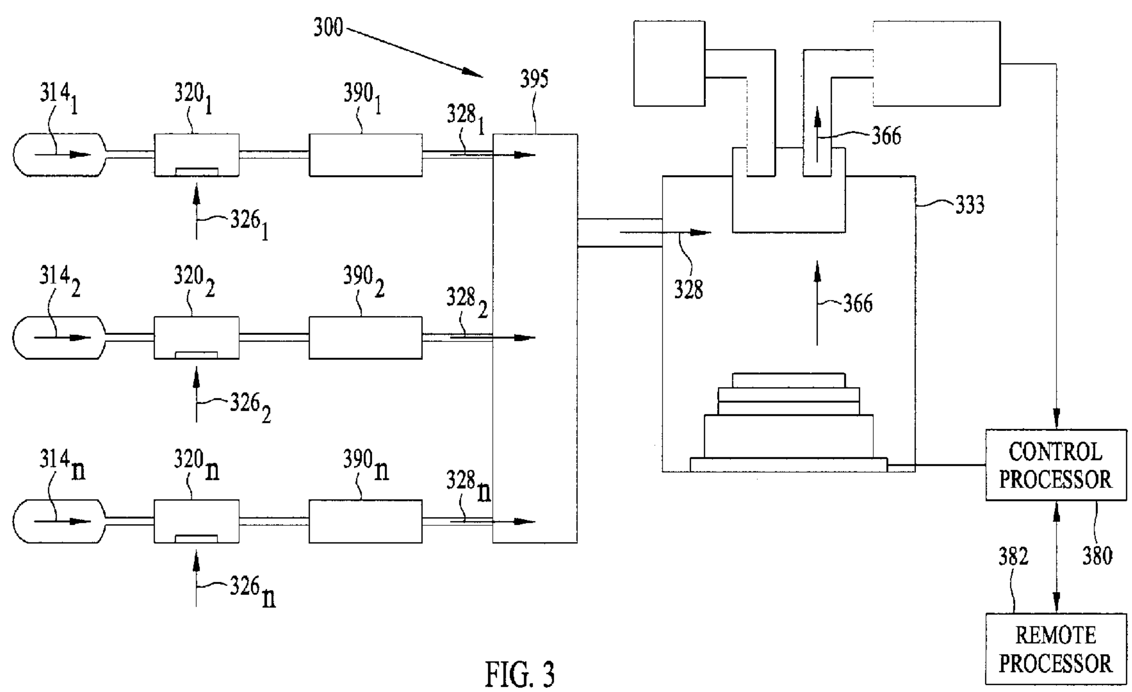
FIG. 3 is a block diagram of the thermoelectrically cooled surface-enhanced Raman spectrometer sensor system having multiple sample collectors.

It is within the embodiment of the thermoelectrically cooled surface-enhanced Raman spectrometer sensor system to have a plurality of sample collectors monitoring the VOCs in the same location. As shown in FIG. 3, analytes $\mathbf{326}_1$, $\mathbf{326}_2$, . . . , $\mathbf{326}_n$ and inert gas $\mathbf{314}_1$, $\mathbf{314}_2$, . . . , $\mathbf{314}_n$ mix to create gas mixtures $\mathbf{328}_1$, $\mathbf{328}_2$, . . . , $\mathbf{328}_n$ in a plurality of manifolds $\mathbf{320}_1$, $\mathbf{320}_2$, . . . , $\mathbf{320}_n$. Gas mixtures $\mathbf{328}_1$, $\mathbf{328}_2$, . . . , $\mathbf{328}_n$ are then preconcentrated in a plurality of thermal desorption tubes $\mathbf{390}_1$, $\mathbf{390}_2$, . . . , $\mathbf{390}_n$, combined in multiplexer 395, and released into sample chamber 333. The spectral data and the corresponding SERS optical emissions signal 366 generated by the presence of analytes $\mathbf{326}_1$, $\mathbf{326}_2$, . . . , $\mathbf{326}_n$ in combined gas mixture 328 may be sent to control processor 380 and/or remote processor 382 for recording and analysis. It is also within the embodiment of the thermoelectrically cooled surface-enhanced Raman spectrometer sensor system to have a plurality of sample collectors monitoring several locations at the same time.

Because all of the steps of using the thermoelectrically cooled surface-enhanced Raman spectrometer sensor system to identify an analyte of interest do not need operator intervention, the thermoelectrically cooled surface-enhanced Raman spectrometer sensor system can be automated with proper computing devices, such as computers, signal transmitters and receivers, computational programs or software to perform the necessary calculations and data comparisons, and other necessary mechanical devices, which can be controlled non-manually when receiving various electromagnetic, electrical, electronic or mechanical commands, instructions or signals. All of the signals and/or instructions from computers or controllers may be communicated via conventional methods such as proper cables, optical fibers, etc. Alternatively, wireless communications are also within the embodiment of the thermoelectrically cooled surface-enhanced Raman spectrometer sensor system.

While the thermoelectrically cooled surface-enhanced Raman spectrometer sensor system is used to provide direct real-time sampling of VOCs, it is not required that the measurements are made continuously. The thermoelectrically cooled surface-enhanced Raman spectrometer sensor system may be operated in many different modes: continuous, semi-continuous, intermittent, batch, or a combination thereof.

Clearly, many modifications and variations of the thermoelectrically cooled surface-enhanced Raman spectrometer sensor system are possible in light of the above teachings. It is therefore to be understood that within the scope of the appended claims the thermo-electrically cooled surface-enhanced Raman spectrometer sensor system may be practiced otherwise than as specifically described.

We claim:

1. A thermo-electrically cooled surface enhanced Raman spectroscopy sensor system, comprising:

at least one means for providing an inert gas;

at least one thermal desorption tube coupled to the at least one means for providing an inert gas, wherein the at least one tube contains an adsorbate for collecting a gas sample and wherein the gas sample and the inert gas mix to create a gas mixture;

a sample chamber coupled to the at least one thermal desorption tube for receiving the gas mixture;

a SERS structure positioned in the sample chamber; and an optical module mounted to the sample chamber for directing an optical excitation signal to irradiate the SERS structure and for receiving a SERS optical emissions signal.

2. The sensor system of claim 1 wherein the optical emissions signal represents an analyte in contact with the SERS structure, wherein the analyte is selected from the group that includes benzene, toluene, ethylbenzene, MTBE, TNT, RDX, cocaine, heroin, saran, xylene, mustard gas, and chlorinated solvents.

3. The sensor system of claim 1 further comprising a multiplexer disposed between the at least one thermal desorption tube and the sample chamber.

4. The sensor system of claim 1 further comprising a manifold, disposed between the means for providing an inert gas and the thermal desorption tube, wherein the manifold has a semipermeable membrane for separating moisture from an analyte and wherein the analyte and the inert gas mix to create the gas sample.

5. The sensor system of claim 1 further comprising a means for generating the optical excitation signal to irradiate the SERS structure, operably coupled to the sample chamber.

6. The sensor system of claim 5 wherein the means for generating an optical excitation signal to irradiate the SERS structure includes a laser.

7. The sensor system of claim 1 further comprising a means for detecting the SERS optical emissions signal, generated in response to the SERS structure being irradiated by the optical excitation signal when an analyte is in contact with the SERS structure.

8. The sensor system of claim 7 wherein the means for detecting a SERS optical emissions signal includes a spectrometer for detecting the spectral characteristics of the optical emissions signal and a means for recording the spectral characteristics.

9. The sensor system of claim 7 further comprising a control processor coupled to the means for detecting the SERS optical emissions signal, wherein the control processor:

positions the SERS structure in the sample chamber;

records and analyzes the SERS optical emissions signal; and generates an alert signal when an analyte is in contact with the SERS structure.

10. The sensor system of claim 9 further comprising a remote processor for receiving the alert signal generated from the control processor.

11. The sensor system of claim 1 further comprising a thermoelectric cooler coupled to the SERS structure, for cooling the SERS structure.

12. The sensor system of claim 11 further comprising a heat exchanger coupled to the thermoelectric cooler, for removing heat energy from the sample chamber.

13. The sensor system of claim 1 further comprising a staging apparatus coupled to the SERS structure, for positioning the SERS structure at selected coordinates.

14. The sensor system of claim 1 wherein the inert gas includes diatomic nitrogen.

15. A method for identifying an analyte of interest, comprising the steps of:

collecting a gas sample in a thermal desorption tube;

mixing the gas sample with an inert gas to create a gas mixture;

contacting a SERS structure with the gas mixture;

irradiating the SERS structure with optical excitation energy for stimulating a SERS optical emission signal if the gas sample contains an analyte that is in contact with the SERS structure;

determining the identity of the analyte from the SERS optical emission signal; and generating an alert signal when an analyte is in contact with the SERS structure.

16. The method of claim 15 further comprising the step of collecting the gas sample through a manifold having a semipermeable membrane.

17. The method of claim 15 wherein the gas sample is obtained from a gaseous environment.

18. The method of claim 15 wherein the gas sample is obtained from a liquid environment.

19. The method of claim 15 wherein the gas sample is obtained from a soil environment.

* * * * *